United States Patent [19]

McDonald et al.

[11] Patent Number: 5,109,835
[45] Date of Patent: May 5, 1992

[54] HEADGEAR FOR CERVICAL TRACTION SYSTEM

[76] Inventors: Philip McDonald, 3326 Elgin Dr.; Newel Kimball, 204 Browning Ave. #5, both of, Salt Lake City, Utah 84109

[21] Appl. No.: 773,978

[22] Filed: Oct. 8, 1991

Related U.S. Application Data

[63] Continuation of Ser. No. 435,272, Nov. 9, 1989, abandoned.

[51] Int. Cl.$^5$ .............................................. A61F 5/08
[52] U.S. Cl. ..................................... 606/241; 602/32
[58] Field of Search ..................... 128/75, 76 R, 84 C, 128/84 R, 87 B, 88, DIG. 23

[56] References Cited

U.S. PATENT DOCUMENTS

| | | | |
|---|---|---|---|
| 923,862 | 6/1909 | Langworthy | 128/75 |
| 1,837,153 | 12/1931 | Ettinger | 128/84 R |
| 2,851,031 | 9/1958 | Ciampa | 128/75 |
| 3,548,816 | 12/1970 | Bond | 128/76 R X |
| 3,871,366 | 3/1975 | Cotrel | |
| 3,888,243 | 6/1975 | Powlan | |
| 3,957,040 | 5/1976 | Calabrese | 128/75 |
| 4,220,147 | 9/1980 | Allen, III | |
| 4,352,352 | 10/1982 | Janovsky et al. | 128/76 R |
| 4,508,109 | 4/1985 | Saunders | |
| 4,793,334 | 12/1988 | McGuinness et al. | |
| 4,987,886 | 1/1991 | McDonald et al. | 128/75 |

OTHER PUBLICATIONS

G. J. Wang, J. T. Moskal, T. Albert, C. Pritts, G. M. Schuch and W. G. Stamp, *The Journal of Bone and Joint Surgery*, "The Effect of Halo-Vest Length on Stability of the Cervical Spine", 1988.
Instructions for Operating the Exo-Bed Traction Unit.
The Lossing Orthopedic Company, "Necktrac TM, Instructions for Treating Patients", 1982.
Med-Trak, Inc., "Clinical Application and General Considerations in the Use of Home Cervical Traction", pp. 1-8.
Dr. John P. Boren, MedTrak Research Labs, Inc., "Conservative, Safe and Effective Treatment of Pain".
Shamrock Medical, Inc., "Econo-Cerv Home Care Supine Cervical Traction".
Hill Laboratories Co., "Hill Cervical Traction Device".
Medipedic, Rigid Cervical Collars.
Medipedic, "Goodley Polyaxial Cervical Traction".
Medipedic, "Bed Cervical Traction" and Door Cervical Traction.
Medipedic, "Head Halters".
Granberg International, "E3000 EZ Tract Information Packet".
The Sukoff Portable Traction Device, Specifications.
Shamrock Medical, Inc., "C-Flex Supine Cervical Traction".
Physical Therapy, vol. 66, No. 8, Aug. 1986, "Goodley Polyaxial Cervical Traction, a New Approach to a Traditional Treatment", by Grace L. Walker, pp. 1255-1259.

*Primary Examiner*—Robert Bahr
*Assistant Examiner*—Linda C. M. Dvorak

[57] ABSTRACT

Headgear for use in cervical traction is described comprising a U-shaped bail member having an arch portion separated by a pair of arm portions, an adjustable front strap assembly which is attachable to the arm portions of the bail at a plurality of locations, and a rear strap assembly which attaches to the distal ends of each of the arm portions of the bail. The headgear works in a manner similar to a four-bar linkage sysstem to grip the head of the user and apply traction thereto. A traction force applied on the arch portion of the bail results in the tightening of the front and rear strap assemblies to the forehead and occipital region of the user's head respectively. The headgear provides efficient traction at all angles between approximately 0 to 60 degrees with the spinal cord, and can be used with traction frames for mobile or immobile patients. The headgear of the present invention substantially improves patient comfort with minimal risk of tissue damage. The headgear is easily adjustable to fit any size or shape of head.

12 Claims, 5 Drawing Sheets

Fig. 6

HEADGEAR FOR CERVICAL TRACTION SYSTEM

This application is a continuation of application Ser. No. 07/435,272 filed Nov. 9, 1989, now abandoned.

BACKGROUND OF THE INVENTION

1. Field of the Invention

The present invention relates to a system useful for applying traction to the cervical spine. More specifically, this invention relates to a headgear or harness useful in a cervical traction system.

2. Brief Description of the Prior Art

Cervical traction is widely accepted as an effective nonoperative treatment of patients with cervical spine disorders such as: 1) cervical spondylosis (arthritis); 2) displacement of intervertebral disc; 3) nerve root compression; and 4) post traumatic derangements. Very often, severe neck pain, limb pain or headaches are associated with these disorders. In each of these cases, cervical traction is applied to provide joint separation, decompression of nerve impingement, neck immobilization, stretching and/or mobilization of the neck muscles.

Ideally, cervical traction for therapeutic purposes should engage only the cervical area and should avoid any painful or damaging involvement of the chin, the mandibular joints, or the temporal areas of the skull. In practice, however, prior art attempts at securing a traction device to the skull have been largely unsuccessful in avoiding such pain or damage.

The headgear used in existing cervical traction devices falls into four basic categories: 1) the "crown" halters; 2) the "chin strap" halters; 3) the track mounted devices; and 4) the skull penetrating devices.

The "chin strap" devices consist of various types of head halters that use chin straps to allow a secure attachment platform for the applied traction. Although these devices are simple in design and relatively inexpensive, the traction forces applied thereto transfer a significant pressure from the chin, directly to the temporomandibular joint. Since pressure at this joint is painful, the patient's tolerance for pain is a limiting factor that determines the amount and duration of traction that can be applied. Typically, the maximum tolerable traction force is about 20 pounds, which is often insufficient for effective separation of the cervical vertebrae. Moreover, severe permanent damage of the temporomandibular joint may occur, resulting in prolonged local pain and/or headaches, and even the need for corrective surgery in some instances.

The "crown" halters are bandage-like devices that cover the ears, the back of the skull, and may also cover the forefront of the head. Traction is applied to the device at a location near the base of the skull.

The main disadvantage of this type of device is the need for an extremely tight attachment to the head before the device is capable of applying traction forces thereto sufficiently great for effective treatment. This extremely tight attachment to the head can cause pain in the form of headaches, etc. Adjusting the tightness for comfort, limits the traction force to values (only up to about 15 lbs.) that are often insufficient for effective treatment. Also, this type of traction device does not permit axial traction to be applied to the patient because of its tendency to slip off the user's head under such forces.

The skull penetrating devices are used in severe neck injuries that require continuous skeletal traction such as for immobilization in fracture cases. The traction forces are applied on various types of tongs that penetrate into the skull, or onto a "halo ring" attached directly to the skull.

The track mounted devices consist generally of two V-shaped arms mounted on a sliding carriage. The V-shaped arms support the back part of the head, with a forehead strap forcing the head into the V-shaped arms. The traction is applied by sliding the V-shaped arms on a fixed track mounted on a bed frame. Movement of the V-shaped arms along the track causes extension of the cervical spine. Compared to the above-mentioned traction devices, the track mounted device is more commonly tolerated by patients, and permits higher amounts of traction force without causing trauma to the chin, forehead or occipital regions of the head. However, the track mounted devices are relatively expensive and cumbersome and do not allow for any type of head rotation. These devices are also unsuitable for other than institutional therapy.

SUMMARY OF THE INVENTION

It is an object of the present invention to provide a cervical traction system which avoids painful or damaging involvement of the chin, mandibular joints, or the temporal areas of the skull.

It is another object of the present invention to provide a cervical traction system which is simple to operate, easy to be attached and removed from the head, and sufficiently adjustable that one size can be adjusted to fit any user.

It is a further object of the present invention to provide a cervical traction system which is of a unified construction suitable for use on both mobile and immobile patients.

It is a further object of the present invention to provide a cervical traction system which fits comfortably to the user's head regardless of the amount of traction force applied thereto in sitting, standing or horizontal positions and at any angle of pull relative to the spine including the axial direction and/or with the head rotated or flexed to either side.

The above and other objects are realized in a specific illustrative embodiment of the headgear which consists of 3 essential parts: a U-shaped bail member having a generally semi-circular arch portion separating a pair of arm portions, a front strap attached to each of the arm portions of the U-shaped bail by means of screws or rivets which allow it to freely rotate relative thereto, and a rear strap member which attaches to the distal ends of the bail arms by means of screws or rivets which also allow the rear strap to rotate relative thereto.

The front and rear straps are attached to the bail through specially designed swivel plates. These swivel plates contain slots through which straps themselves are inserted. The straps can be adjusted to any desired position to accommodate the particular size and shape of the user's head. The front strap swivel plates can be attached to the U-shaped bail at various locations along the bail arms. The relative location of the attachment of the front swivel plates to the bail arm directly affects the gripping forces applied to the head when traction forces are pulled on the headgear.

To attach the headgear, the front strap is placed along the forehead of the user and the back straps are placed around the back of the user's head close to the neck in the recess of the occipital area. Traction forces are then applied to a strap which is attached to the arch portion of the U-shaped bail at a predetermined location.

The headgear works on the basis of a four-bar linkage. An upward force applied to the arch portion of the U-shaped bail first causes the headgear to tighten securely around the head at the areas contacted by the straps. Then, continued force results in effective traction of the neck and spine. Because of the shape of the bail arms and the location of the straps, gripping force is applied mainly to the front and back of the user's head, leaving relatively small amounts, if any, of the gripping force to be applied to the sides of the user's head.

Upward motion of the bail arch forces the pivot point between the back strap and the bail to move in the direction of the distal end of the bail arch. Since the back strap attached next to the occipital region of the head begins to push the head in a rotational direction which tends to cause the head to rotate slightly forward, the front strap is necessary to prevent the head from rotating out of contact with the back strap. The inward rotation of the front strap and the back strap caused by the upward movement of the arch portion of the bail, and the upward motion of the pivot point between the bail and the front strap, causes a tightening of the straps around the head of the user. Once the front strap tightens around the forehead to prevent the head from rotating away from the force applied by the back strap to the occipital area thereof, the entire head is pulled in the direction of the pulling force on the bail arch. A body weight and/or resistance force applied to the user's shoulders or other portions of the body results in an effective traction of the neck and spine areas.

The straps and swivel plates of the device may be padded or otherwise modified to conform to the user's head. The arm portions of the bail, and the swivel plates may be curved to a degree sufficient to allow comfortable fit around and next to the user's head. The bail and swivel plate may be formed of any plastic, metal or composite material which is sufficiently strong to withstand commonly required traction forces. The straps may be made of any non-stretching material and may be adjustable by any suitable means, such as hook and loop type fasteners.

BRIEF DESCRIPTION OF THE DRAWINGS

The above and other objects, features and advantages of the invention will become apparent from a consideration of the following detailed description presented in conjunction with the accompanying drawings in which:

FIG. 3b is a cross-sectional view of an alternative embodiment of FIG. 3a;

DETAILED DESCRIPTION OF THE INVENTION

Figure 1:
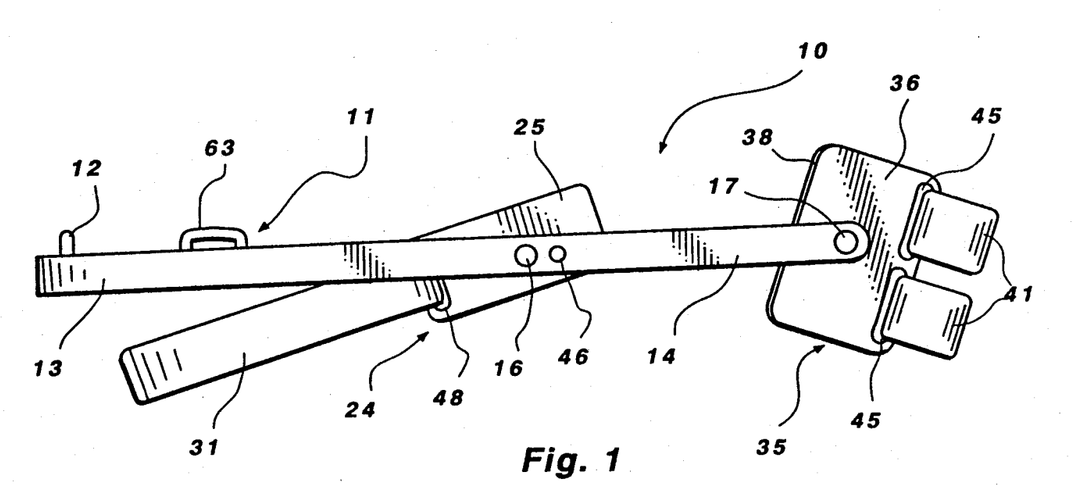
FIG. 1 is a side elevational view of the headgear embodying the principles of the present invention.

Referring to FIG. 1, there is shown a headgear 10 made in accordance with the principles of the present invention. The headgear 10 comprises three main structural assemblies which function similarly to separate linkages in a four bar linkage system to securely grip and pull the head away from the neck and spine of a user when used, such as for example, in conjunction with a traction frame (such as shown at 52 in FIG. 6) in a manner which will be explained momentarily.

Figure 2:
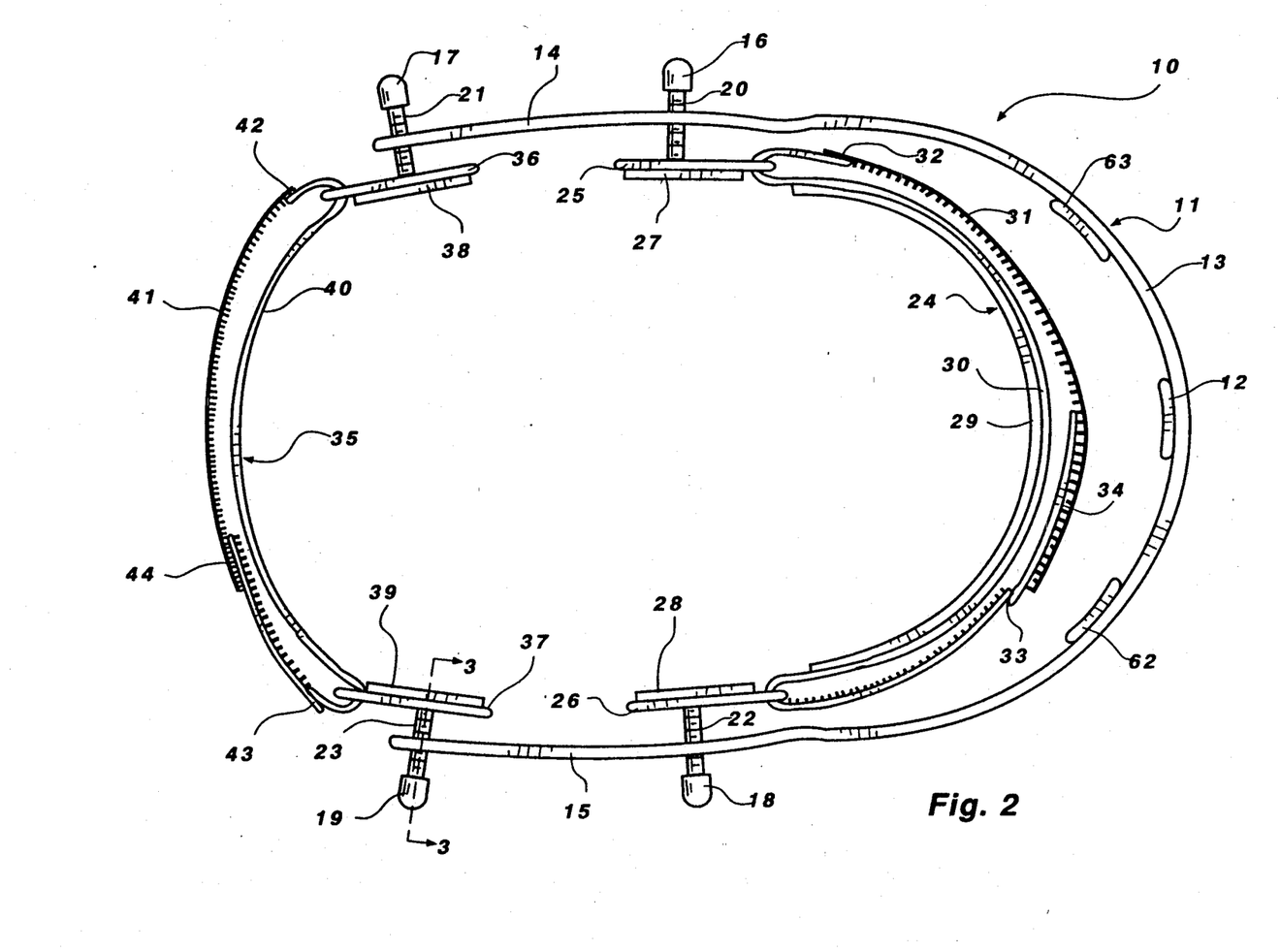
FIG. 2 is a plan or top view of the headgear as shown in FIG. 1.

The first major portion of the headgear 10 is the U-shaped bail 11. As best seen in FIG. 2, the U-shaped bail 11 is an integral unit having a central generally semi-circularly shaped arch 13 and, extending from either end of the arch, slightly curved arm members 14 and 15. Arm members 14 and 15 can either be formed as continuations of arch portion 13 or can be attached thereto by conventional means such as by welding, screws, bolts, and the like. Preferably, as shown in FIG. 2, bail 11 consists of a single unit having three portions, i.e. a central arch 13 terminating in slightly curved arm members 14 and 15. The bail arch 13 can have an attachment device such as pull ring 12 secured thereto in order to allow for simple attachment of a tensioning strap (such as shown at 60 in FIG. 6) thereto as will be later explained. The bail may be formed of any material such as plastic, metal, graphite, wood, etc. which is capable of rigidly withstanding forces common to tractioning devices of this nature. For example, traction forces of up to 50 pounds.

The second major portion of the headgear 10 is the rear strap assembly 35. The rear strap assembly 35 includes a pair of rear swivel plates 36 and 37, and a pair of rear straps 41. Each rear swivel plate 36 and 37 comprises at least one but preferably two slots 45 through which rear straps 41 may be inserted. Although straps 41 may be adjustable by any well-known fastening device such as snaps, ties, pins, buckles, etc., the most preferred embodiment includes a loop and hook type fastener. Each strap 41 is comprised of a loop portion 40 and a hook portion 44, which, when connected, have a total length which extends twice the distance between swivel plates 36 and 37. The hook portion and strap 44 may be attached to the loop portion 40 by stitching, thermal binding or the like as shown at 42, and a loop portion of strap 40 may be inverted and attached to an opposite end thereof by means of stitching or thermal bond as shown at 43, all in a manner as is well-known.

A third major portion of the headgear 10 is the front strap assembly 24. The front strap assembly 24 includes front swivel plates 25 and 26 each having slot shaped openings 48 through which a hook and loop strap 31 is inserted. Strap 31 includes loop portion 30 and hook portion 34 arranged and oriented for interfastening at seam points 32 and 33 in the manner identical to the rear straps 41 as explained above. Each of the straps 41 and 31, along with each of the swivel plates 25, 26, 36, 37, may have pads 29, 27, 28, 38, and 39 respectively, attached to the inside surfaces thereof. These pads come in contact with the user's head when the headgear 10 is placed thereon, and tend to cushion, and therefore render more comfortable, the gripping forces transmitted through the headgear 10 to the user's head.

The front and rear strap assemblies 24 and 35 respectively are rotatably attached to the bail 11 by insertion of screws or rivets 20, 21, 22 and 23 through openings in the bail arms 14 and 15. Each of the swivel plates 25, 26, 36 and 37 being attached to the bail arms 14 and 15 in an identical manner.

Figure 3A:
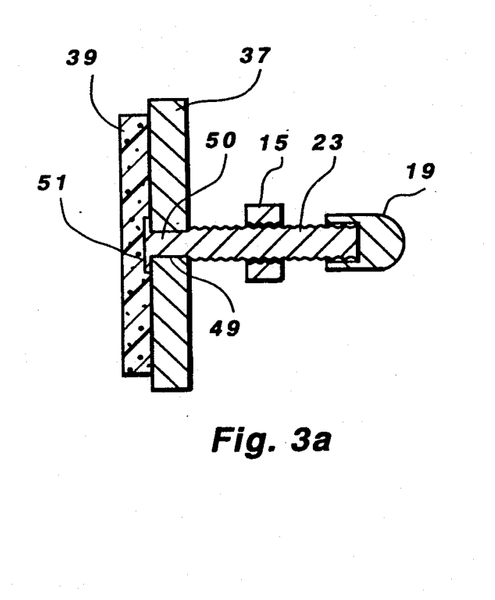
FIG. 3a is a cross-sectional view taken along line 3—3 of FIG. 2.
Figure 3B:
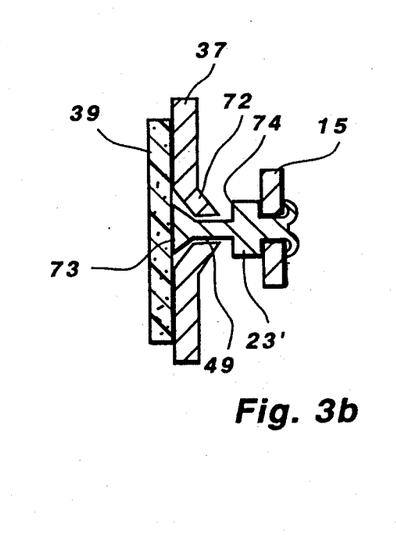

FIGS. 3a and 3b show cross sections taken through swivel plate 37. In FIG. 3a, screw 23 passes through hole 49 in swivel plate 37 and is secured in place by flange 51. The portion 50 of screw 23 which is adjacent to hole 49, is smooth thereby allowing free rotation of swivel plate 37 relative thereto. Screw 23 then passes through the threaded opening in bail arm 15 and is covered by cap 19 to prevent injury to the user. It is equally contemplated that simple rivets be used in place of the screws 20, 21, 22 and 23. The rivets holding the bail arms 14 and 15 in rotational connection with the swivel plates 25, 26, 36 and 37. In FIG. 3b, a rivet 23' passes through hole 49 in swivel plate 37 and is secured in place by the conically shaped flange 73. The portion 74 of the flange 23' which is adjacent to hole 49, is smooth thereby allowing free rotation of the swivel plate 37 relative thereto. Also, because of the conically shaped flange 73 and the similarly shaped indentation 72 of the swivel plate 37, the rivet 23' also allows the plate 37 to gimbal in all directions relative to the bail arm 15. Rivet 23' then passes through the opening in bail arm 15 and is secured in place thereto as by common riveting methods. The shoulder 74 of the rivet works in conjunction with conically shaped flange 73 to prevent the rivet from extending further through swivel plate 37 than is desired, e.g., to prevent the conically shaped flange 73 from being pushed through the pad 39 and become in contact with the user's head.

Bail arms 14 and 15 may comprise other openings such as opening 46 shown in FIG. 1 to allow the point of attachment of swivel plates 25 and 26 to be adjustable along the length thereof.

Figure 4:
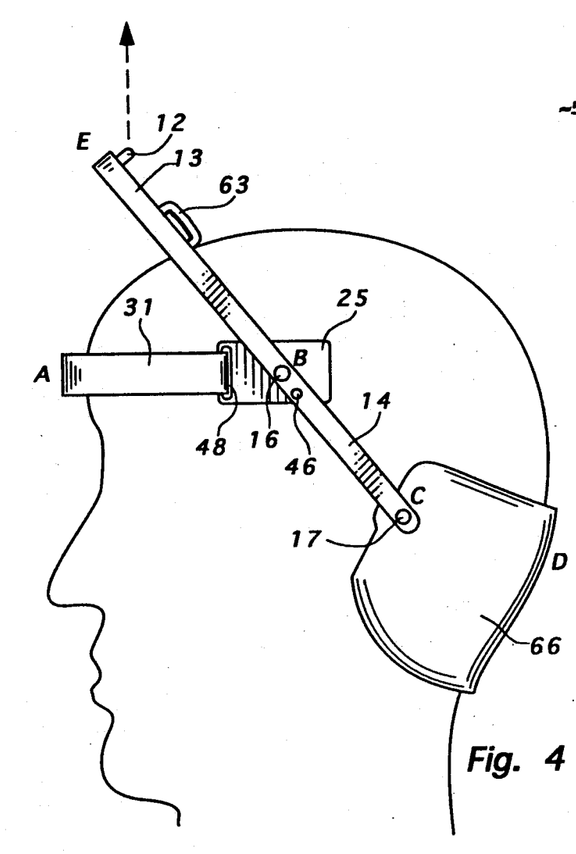
FIG. 4 is a side elevational view of another embodiment of the headgear according to the principles of the present invention attached to a user's head.

Several modifications to the basic structure of the headgear 10 are contemplated and are felt to fall within the scope of the present invention. For example, as shown in FIG. 4, the rear strap assembly 35 may be replaced with a form-fitting neck piece 66 comprising a moldable plastic material which can be conformed to the contours of the occipital area of the intended user's head. The neck piece 66 may also be lined with a pad or cushion material in the manner already explained above. Also, the front strap assembly 24 may be similarly modified to include a form-fitting piece (not shown) which can be conformed to the contours of the intended user's forehead.

Figure 5:
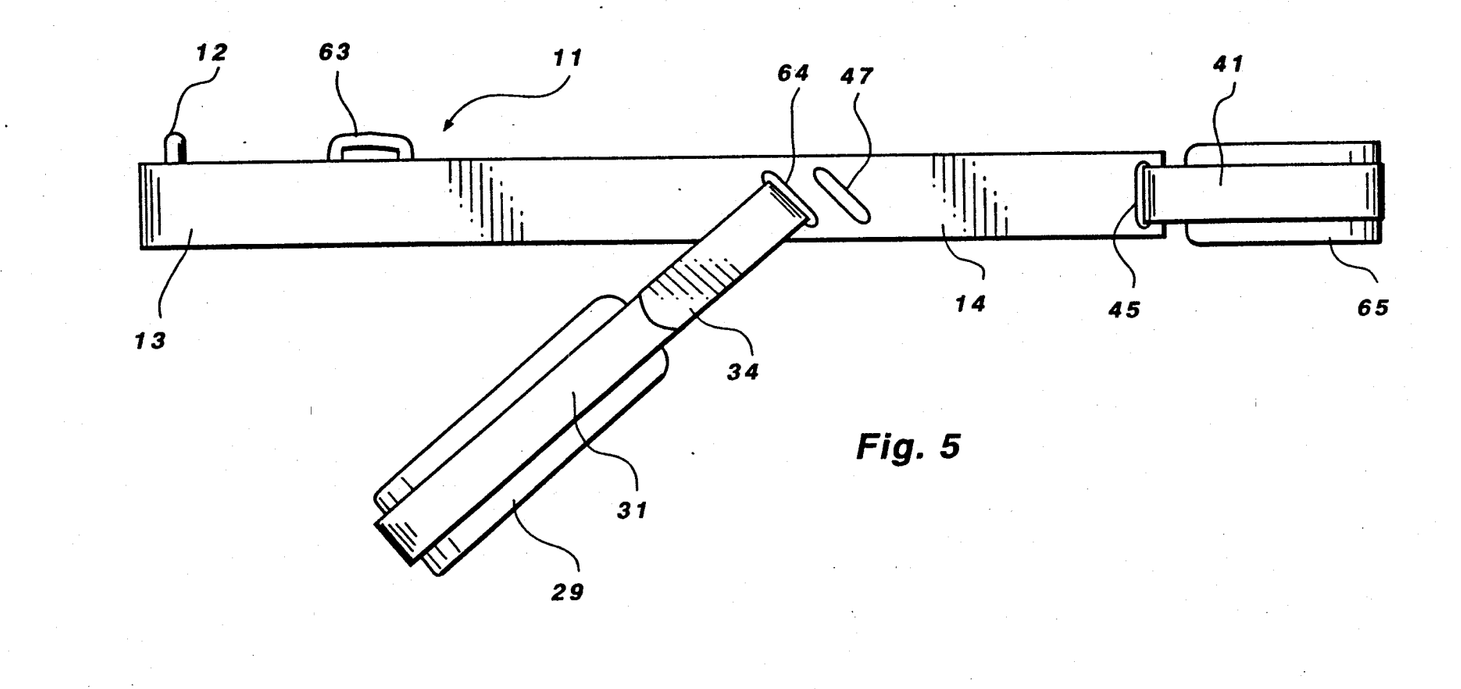
FIG. 5 shows a further embodiment of the headgear made according to the principles of the present invention.

FIG. 5 shows another example of a preferred modification to the headgear 10. In FIG. 5, the swivel plates 25, 26, 36, and 37 have been eliminated. The straps 31 and 41 insert directly through slots such as slot 64 and 45 in bail arms 14 and 15. As can be seen, the slots (shown at 64 and 47) used to attach the front strap 31 to the bail arms 14 and 15, are slanted at an angle of approximately 45 degrees. This is done to allow the straps 31 to pull evenly through the slots when the headgear 10 is in its tractioning position on the head of a user. Also, strap 41 is shown to contain a cushion or pad 65 lining its interior surface in the manner as has been explained above with respect to pad 29.

Figure 6:
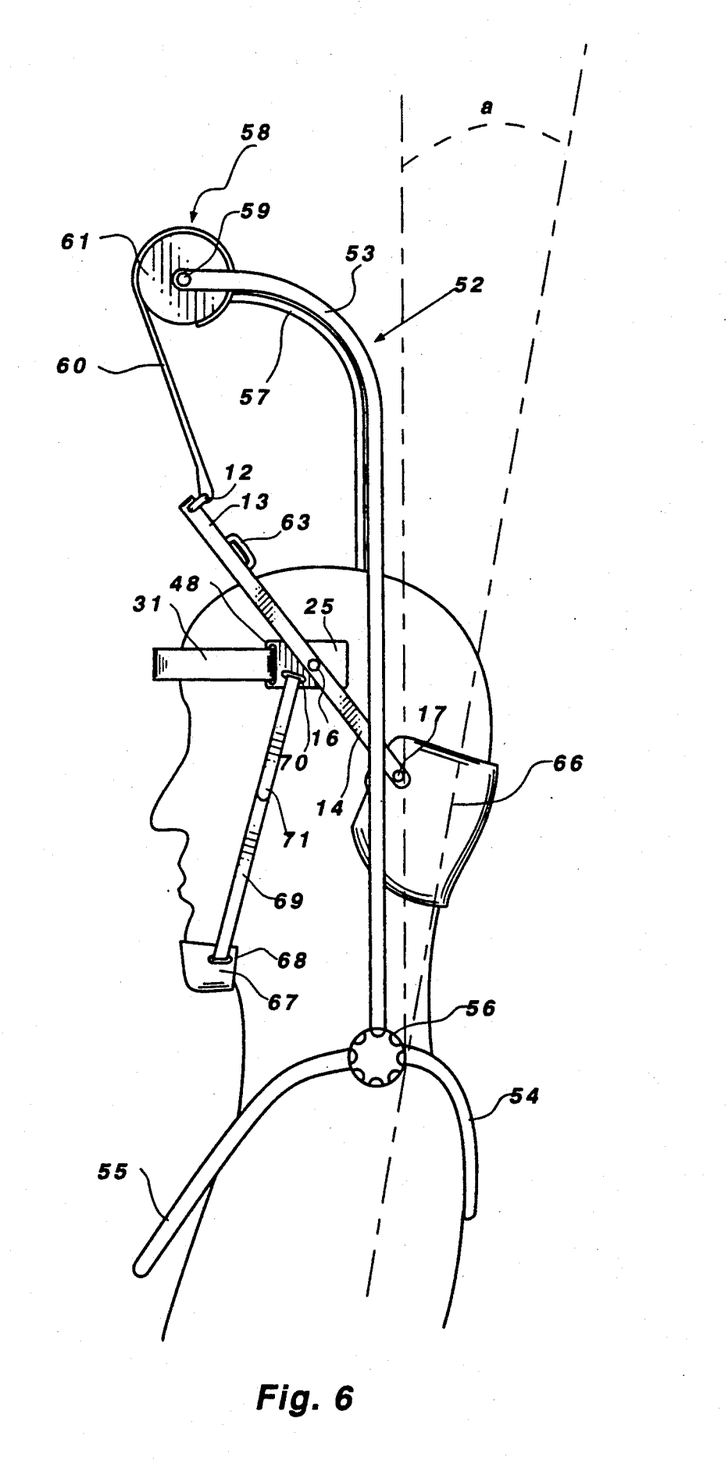
FIG. 6 shows another embodiment of the headgear according to the principles of the present invention attached to a user's head in conjunction with a traction frame.

FIG. 6 shows another embodiment of the headgear 10 which is felt to fall within the scope of the present invention. The headgear 10 is similar to that shown in FIG. 4, with the addition of a chin strap 69 which extends from a slot 70 in swivel plate 25 (and a similar slot in swivel plate 26 on the opposite side of the headgear) down to a slot 68 in a chin cup 67. The strap 69 doubles back and attaches to itself at 71 by means of hook and loop fastening material or the like. Chin strap 69 can be very useful in preventing the front strap 31 from slipping off from a user with an extremely rearward sloping forehead.

FIG. 6 also shows the headgear 10 of the present invention being used in conjunction with a traction frame 52. The frame 52 as shown is merely exemplary of frames which may be used in conjunction with the present invention. It is to be understood, however, that the present invention may be used in conjunction with any traction force generating system including weights and/or the user's own body weight. The frame 52 is formed of generally A-shaped framing members 53 which extend in a curved fashion above the user's head to secure a spring assembly 58 in the correct position for applying tractional forces through tensioning strap 60 which is attached to pulling ring 12 of the headgear 10. Spring housing 61 encloses a tensioning spring which can be adjusted by means of spring tensioning arm 57 to generate the desired tractioning force. The opposite ends of A-frame members 53 extend to the shoulder area of the user and attach to rear shoulder harness 54 and front shoulder harness 55 through adjusting knob 56. Adjusting knob 56 allows the A-frame members 53 to be adjusted to extend at the predetermined angle from the user's shoulder. A frame assembly suitable for use with the present invention is the subject of applicant's co-pending patent application Ser. No. 07/433,751, filed Nov. 8, 1989 and now abandoned and issued as U.S. Pat. No. 4,987,886.

MODE OF OPERATION

Figure 7:
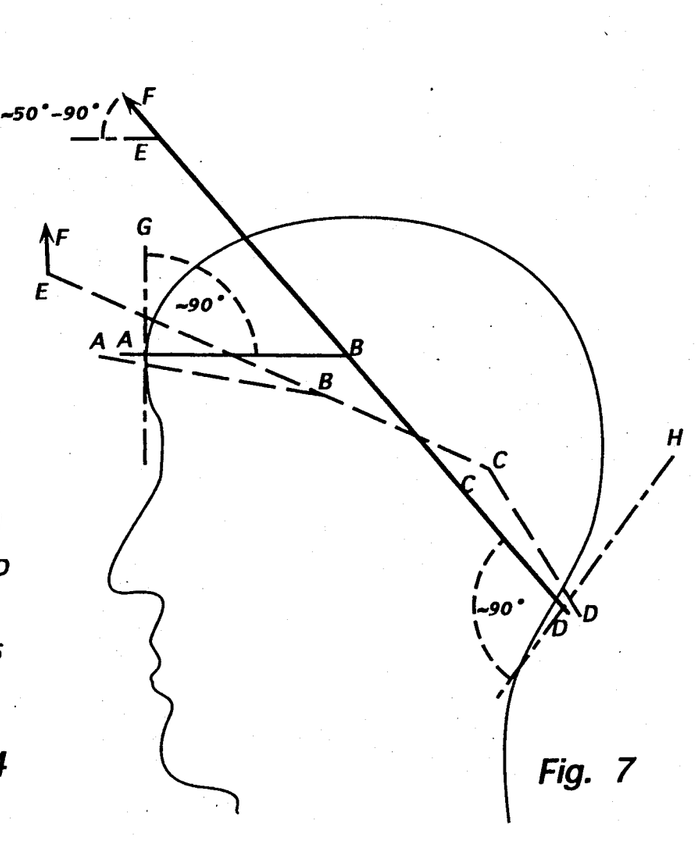
FIG. 7 shows a schematic of the motion of the headgear of the invention caused by traction.

FIG. 7 shows a schematic diagram of the motion of the headgear 10 when tractioning the neck and spine of the user. For convenience in reference, points A, B, C, D and E correspond with the points shown on headgear 10 of FIG. 4. Although the user's head and the headgear 10 are three-dimensional, their symmetry allows the schematic showing the motion of the headgear to be simplified and shown as a two-dimensional system having a central plane which passes through the nose, the center of the forehead, and the occiput of the user's head as shown in FIG. 7.

The headgear 10 is analogous to a four-arm linkage mechanism, in which the four arms AB, BC, CD and DA (the link DA in actuality not being part of the headgear 10 but instead constituting the user's head itself). When the headgear 10 is first placed on the head of the user, the linkages AB, BC, CD and DA (as shown by the long dashed lines) are lined in a nearly linear fashion allowing the distance between points D and A to be as great as possible so that the headgear 10 can be easily slid into position on the head. The connecting link BC is part of the bail 11 (it is in fact the representations of the bail arms 14 and 15). This link BC extends to point E to include a lever arm EB (point E being the most proximal point on the bail arch 13) where the active traction force is applied. Lever arm EB is therefore not necessarily part of the four bar linkage itself, but instead is attached thereto through point B and is used to apply traction forces thereto. In the motion of the three mobile arms therefore, the link BC is the driving link, i.e., force applied at point E causes the driving link BC to translate or rotate. Rotation causes point A and point D to be pulled in toward the head. Once point A, which represents the distal most point of the front strap 31, and point D, which represents the distal most point of rear strap 41, snugly position themselves against the forehead and occiput respectively of the user's head, they are effectively fixed in position. Further force applied at point E can cause no more rotation of linkage BC unless the entire head rotates therewith. The direction of the applied traction force F can cover a range of angles between approximately 0 to 60 degrees forward of the plane of the user's vertebrae, the angle of application of the tractional force determining the flexion angle generated in the spine. The particular angle of application of the tractional force chosen will depend on the desired flexion angle "a" (best shown in FIG. 6, the flexion angle being the angle made between the spine at the shoulders and the spine of the neck) and translational traction force to which the user is to be subjected. (As can be readily determined by one of ordinary skill in the art, the component of force F applied parallel to linkage BC forcing the head and neck to move to the desired flexion angle and the component of the force F perpendicular to BC tending to tighten the linkage securing it to the user's head.)

The length of linkage BC can be adjusted on the headgear 10 by changing the attachment points of swivel plates 25 and 26 along the bail arms 14 and 15.

As can be seen in FIG. 7, when the traction force is applied at point E, linkages AB and CD move in toward the head until points A and D become fixed at the forehead and occipital area respectively. Once points A and D become fixed, further traction force causes the head and neck to move to the desired flexion angle a, and the neck spinal area to be put into a state of traction.

The final position of linkages AB and CD is approximately perpendicular to the frontal and occipital planes (as shown by the dot dash lines G and H respectively). It is important for correct tractioning of the head and for the comfort of the user, that the linkages AB and CD achieve this approximately perpendicular position. It is important therefore that linkages AB, BC, and CD all be adjustable in length to allow the device to be correctly fitted to the user's head.

Linkage AB represents the front strap 31 of the headgear 10 and linkage CD represents the rear strap 41 of headgear 10, both straps being easily adjustable to the proper length for any size of head.

Linkage BC represents the portion of the bail arms 14 or 15 which is located between the attachment points of the front and rear strap assemblies 24 and 35 respectively. Point B represents the location of attachment of the front strap assembly 24 to the bail arms 14 or 15, and as best seen in FIGS. 1 and 4, can be adjusted by moving the bolts 20 and 22 into different bolt openings such as opening 46. Any number of bolt holes 46 may be placed along the bail arms 14 and 15 in order to provide the needed adjustability to the attachment location of the front strap assembly 24. It is, however, contemplated that the length of linkage BC may be standardized for simplicity of design and use if so desired.

As can be seen in FIGS. 1, 2, 4 and 6, the bail arch 13 may have other pulling rings such as 62 and 63 attached thereto for receiving tensioning forces. Tensioning forces pulled at these locations cause the headgear to traction the user's head in a way which is not symmetrical. The use of traction forces in an asymmetrical location on the arch 13, such as at point 62 as shown in FIG. 2, has the same effects as if traction were applied at point 12 with the addition of a second rotational moment being applied to the head (a rotational moment which tends to force one side of the user's head toward the shoulder).

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

We claim:

1. Headgear comprising
    integrated first linkage means and lever arm means comprising a U-shaped bail having a central, generally semi-circularly shaped arch portion adapted to fit about the head of a user and terminal arm members extending from either end of said arch portion, each of said arm members having a proximal end at the juncture of said arm member with said end of said arch portion and an opposing distal end, said arm members forming said first linkage means,
    second linkage means comprising two swivel plates, each of which rotatably interconnects said first linkage means at the proximal end portion of one of said arm members, and a strap attached to said swivel plates and extending therebetween, said strap being adapted to engage the forehead of a wearer,
    third linkage means adapted to engage the occiput of a wearer, interconnecting said first linkage means at the distal end portion on each of said arm members,
    whereby, said headgear cooperates with the head of a user to form a four bar linkage with the portion of said arm members between the point of attachment of said second linkage means and said third linkage means being the first link of the four bar linkage and whereby forces applied to said lever arm means are transferred to said four bar linkage.

2. The headgear according to claim 1 wherein the central generally semi-circularly shaped arch portion of said U-shaped bail further includes means, disposed off-center on said arch portion, for attaching said headgear to a cervical traction system, whereby the user's head is tractioned asymmetrically.

3. The headgear of claim 1 further comprising a connecting rod disposed between each swivel plate of said second linkage means and said first linkage means, whereby each of said swivel plates is spaced from and rotatably connected to said first linkage means.

4. The headgear of claim 3 wherein said connecting rods comprises a screw whereby the swivel plates of said second linkage means are variably spaced from said first linkage means.

5. The headgear according to claim 3 wherein said first linkage means contains means for accommodating said connecting rods at a plurality of locations on the proximal end portion of each of said arm members, whereby the length of said first link is adjustable.

6. The headgear according to claim 3 wherein said connecting rod includes a substantially conical flange and said swivel plate includes a substantially conical indentation into which said flange is placed, enabling said swivel plate to gimbal relative to said first linkage means.

7. The headgear according to claim 1 wherein the strap of said second linkage means is adjustable.

8. The headgear according to claim 1 wherein said third linkage means further comprises swivel plate means, and a strap connected to said swivel plate means, and said swivel plate means being connected to said first linkage means.

9. The headgear according to claim 8 wherein the strap of said third linkage means is adjustable.

10. The headgear of claim 8 further comprising a connecting rod disposed between said swivel plate means of said third linkage means, and said first linkage means, whereby said swivel plate means is spaced from and rotatably connected to said first linkage means.

11. The headgear according to claim 10 wherein said connecting rod includes a substantially conical flange and said swivel plate means includes a substantially conical indentation into which said flange is placed, enabling said swivel plate means to gimbal relative to said first linkage means.

12. The headgear of claim 10 wherein said connecting rod comprises a screw whereby the swivel plate means of said third linkage means is variably spaced from said first linkage means.

* * * * *